United States Patent
Kostromine et al.

(10) Patent No.: US 9,273,213 B2
(45) Date of Patent: Mar. 1, 2016

(54) SPECIAL UV ABSORBERS FOR CURABLE UV-PROTECTIVE COATINGS

(75) Inventors: Serguei Kostromine, Swisttal-Buschhoven (DE); Timo Kuhlmann, Leichlingen (DE); Rafael Oser, Krefeld (DE)

(73) Assignee: Covestro Deutschland AG, Leverkusen (DE)

( * ) Notice: Subject to any disclaimer, the term of this patent is extended or adjusted under 35 U.S.C. 154(b) by 492 days.

(21) Appl. No.: 13/879,044

(22) PCT Filed: Oct. 7, 2011

(86) PCT No.: PCT/EP2011/067572
§ 371 (c)(1),
(2), (4) Date: Apr. 12, 2013

(87) PCT Pub. No.: WO2012/049091
PCT Pub. Date: Apr. 19, 2012

(65) Prior Publication Data
US 2013/0236743 A1    Sep. 12, 2013

(30) Foreign Application Priority Data
Oct. 12, 2010    (EP) .................................... 10187268

(51) Int. Cl.
*C07D 251/24* (2006.01)
*C08K 5/3492* (2006.01)
*C09D 5/32* (2006.01)
*C07B 63/04* (2006.01)
*C09K 15/30* (2006.01)
*C08K 5/00* (2006.01)

(52) U.S. Cl.
CPC . *C09D 5/32* (2013.01); *C07B 63/04* (2013.01); *C07D 251/24* (2013.01); *C08K 5/3492* (2013.01); *C09K 15/30* (2013.01); *C08K 5/005* (2013.01); *C08K 5/0025* (2013.01)

(58) Field of Classification Search
None
See application file for complete search history.

(56) References Cited

U.S. PATENT DOCUMENTS

| | | | |
|---|---|---|---|
| 4,101,513 A | 7/1978 | Fox et al. | |
| 4,185,009 A | 1/1980 | Idel et al. | |
| 5,041,313 A | 8/1991 | Patel | |
| 5,235,026 A | 8/1993 | Wulff et al. | |
| 5,367,044 A | 11/1994 | Rosenquist | |
| 5,391,795 A | 2/1995 | Pickett | |
| 5,538,840 A | 7/1996 | Van Toan et al. | |
| 5,679,820 A | 10/1997 | Pickett et al. | |
| 5,869,185 A | 2/1999 | Bahr et al. | |
| 5,981,073 A | 11/1999 | Pickett et al. | |
| 6,013,704 A | 1/2000 | Hayoz et al. | |
| 6,225,384 B1 | 5/2001 | Renz et al. | |
| 6,228,973 B1 | 5/2001 | McCloskey et al. | |
| 6,350,521 B1 | 2/2002 | Chen et al. | |
| 6,500,887 B1 | 12/2002 | Tobita et al. | |
| 6,613,869 B1 | 9/2003 | Horn et al. | |
| 6,720,072 B1 | 4/2004 | Hinterwaldner et al. | |
| 2001/0039341 A1 | 11/2001 | Fletcher et al. | |
| 2002/0120092 A1 | 8/2002 | Kratschmer et al. | |
| 2004/0164446 A1 | 8/2004 | Goossens et al. | |
| 2005/0250915 A1 | 11/2005 | Heuer et al. | |
| 2006/0052491 A1 | 3/2006 | Braig et al. | |
| 2006/0234061 A1 | 10/2006 | Buckel et al. | |
| 2007/0104956 A1 | 5/2007 | Grandhee | |
| 2007/0237967 A1 | 10/2007 | Buckel et al. | |
| 2008/0017071 A1 | 1/2008 | Moebus et al. | |
| 2008/0081896 A1 | 4/2008 | Heuer | |
| 2009/0130489 A1 | 5/2009 | Stollwerck et al. | |
| 2009/0258978 A1 | 10/2009 | Ruediger et al. | |
| 2012/0094127 A1 | 4/2012 | Meyer Zu Berstenhorst et al. | |

FOREIGN PATENT DOCUMENTS

| | | |
|---|---|---|
| DE | 25 00 092 A1 | 7/1976 |
| DE | 2804283 A1 | 8/1978 |
| DE | 42 40 313 A1 | 6/1994 |
| DE | 19739781 A1 | 3/1998 |
| DE | 19846660 A1 | 4/2000 |
| DE | 19 943 642 A1 | 3/2001 |
| DE | 60307122 T2 | 11/2006 |
| DE | 102006016642 A1 | 10/2007 |
| DE | 102007050192 A1 | 4/2009 |
| EP | 0517044 A2 | 12/1992 |
| EP | 0 570 165 A2 | 11/1993 |
| EP | 0706083 A1 | 4/1996 |
| EP | 0931820 A1 | 7/1999 |
| EP | 1308084 A1 | 5/2003 |
| EP | 1506249 A1 | 2/2005 |
| EP | 1582549 A1 | 10/2005 |
| EP | 2427440 A1 | 3/2012 |
| WO | WO-99/26934 A1 | 6/1999 |
| WO | WO-99/26935 A1 | 6/1999 |
| WO | WO-00/66675 A1 | 11/2000 |
| WO | WO-0226862 A1 | 4/2002 |
| WO | WO-0344099 A1 | 5/2003 |
| WO | WO-2004/035474 A1 | 4/2004 |
| WO | WO-2005/030856 A1 | 4/2005 |
| WO | WO-2005113639 A1 | 12/2005 |
| WO | WO-2006/008120 A1 | 1/2006 |
| WO | WO-2006/108520 A1 | 10/2006 |
| WO | WO-2008037364 A1 | 4/2008 |
| WO | WO-2008/071363 A2 | 6/2008 |
| WO | WO-2008/109072 A1 | 9/2008 |

OTHER PUBLICATIONS

International Search Report for PCT/EP2011/067572 mailed Nov. 3, 2011.

*Primary Examiner* — Ramsey Zacharia
(74) *Attorney, Agent, or Firm* — Drinker Biddle & Reath LLP

(57) ABSTRACT

The present invention relates to organic UV absorbers which have two or more polymerizable acrylate or methacrylate groups in the molecule, to coating compositions comprising such UV absorbers, and also to coatings produced therefrom and to substrates coated therewith.

16 Claims, No Drawings

SPECIAL UV ABSORBERS FOR CURABLE UV-PROTECTIVE COATINGS

RELATED APPLICATIONS

This application is a national stage application (under 35 U.S.C. §371) of PCT/EP2011/067572, filed Oct. 7, 2011, which claims benefit of European application 10187268.7, filed Oct. 12, 2010, incorporated herein by reference.

The present invention relates to organic UV absorbers which have two or more polymerisable acrylate or methacrylate groups in the molecule, to coating compositions comprising such UV absorbers, and also to coatings produced therefrom and to substrates coated therewith.

For outside applications, transparent plastics articles, such as, for example, sheets, films or extruded moulded articles, must be protected especially against aggressive solar radiation by means of UV protection and against mechanical effects by the provision of scratch-resistant properties. A conventional method of achieving such protection is to provide the upper, and sometimes the only, protective layer, which must be scratch-resistant, with an additional UV-protective function and to that end to provide it with a considerable amount of UV absorbers (see DE-A 10 2006 016 642). However, conventional UV absorbers act as plasticisers in the protective layers and reduce the mechanical resistance of the layer.

Typical UV absorber classes are, for example, biphenyl-substituted triazines (see WO-A 2006/108520). This substance class exhibits an outstanding absorption efficiency at 320-380 nm and at the same time very high inherent UV stability (WO 2000/066675 A1, U.S. Pat. No. 6,225,384).

In addition, there are not insignificant compatibility problems between the UV absorber and the components of the coating composition. For scratch-resistant sol-gel coatings, which exhibit extraordinarily good scratch resistance, it is, for example, very difficult to find a compatible UV absorber because UV absorbers, which are generally highly aromatic, are sparingly soluble in the polar sol-gel lacquer mixtures. Although the solubility of UV absorbers, such as, for example, of the class of the 2-hydroxy-benzophenones (U.S. Pat. Nos. 5,679,820; 5,391,795) in sol-gel lacquer systems could be increased by purposively modifying the UV absorber molecules by incorporating trialkoxysilane groups, the introduction of such large organic molecules into an inorganic silica matrix in a significant concentration of several percent by weight can, however, lead to reductions in the hardness and scratch resistance of the coating, so that the optimum potential of sol-gel lacquer coatings in respect of their mechanical resistance can no longer be fully utilised.

A possible solution to this problem might be to separate layers having UV and mechanical protective functions, the first "soft" purely organic layer containing sufficient UV absorber and the second, outer layer, which is as hard as possible, protecting against scratches and abrasion. Such approaches are already known. For example, the layer of adhesion promoters (primers) in sol-gel lacquer coatings is often provided with UV absorbers (see e.g. U.S. Pat. Nos. 5,041,313; 5,869,185; 5,981,073; 6,350,521; DE 10 2007 050192). Such primer layers comprise substantially soluble polymethacrylates and are generally thin but at the same time must not be too soft. The latter again has the result that the necessary amount of the conventional UV absorber that would be required to achieve adequate UV protection cannot be added to such layers. It is then attempted to compensate for the resulting lack of UV protection of the individual layer by adding UV absorbers to all the protective and intermediate layers that are present (primer and clear lacquer layers, see e.g. U.S. Pat. No. 4,410,594) and optionally also to the substrate that is to be protected (e.g. US-A 2009-0258978), which again results in the problem of the UV absorber's acting as a plasticiser. Moreover, because conventional UV absorbers are crystalline organic substances which do not themselves have film-forming properties and must therefore be dissolved in a film-forming binder, separate UV-protective primer layers are generally too thick and often too soft to be able to make any substantial contribution to the UV protection.

Accordingly, there was a continued need for suitable UV absorbers which can be used to produce primer layers with a satisfactory UV-protective action and which do not have the disadvantages mentioned hereinbefore.

The object underlying the present invention was, therefore, to find UV absorbers with which thin and not too soft primer layers with a satisfactory UV-protective action can be produced, so that the further addition of UV absorbers to the scratch-resistant top layer is not necessary or the further addition of UV absorbers to the scratch-resistant top layer is no longer necessary in such amounts that the scratch-resistant function thereof is impaired.

The object has been achieved by the present invention by the provision of UV absorbers of the substance class of the s-triazines, preferably biphenyl-substituted s-triazines, which have two or more polymerisable acrylate and/or methacrylate groups, which are attached to an open-chain substituent of the hard aromatic colourant core.

The present invention provides compounds of the general formula (I)

wherein
A represents

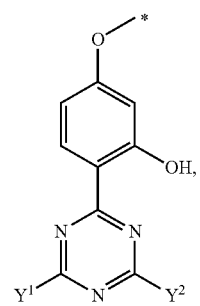

wherein
$Y^1$ and $Y^2$ independently of one another represent substituents of the general formula

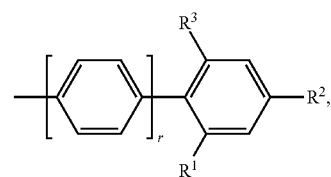

wherein
r represents 0 or 1, preferably 1,
$R^1$, $R^2$, $R^3$ independently of one another represent H, OH, $C_{1-20}$-alkyl, $C_{4-12}$-cycloalkyl, $C_{2-20}$-alkenyl, $C_{1-20}$- alkoxy, $C_{4-12}$-cycloalkoxy, $C_{2-20}$-alkenyloxy, aralkyl, halogen, —C≡N, $C_{1-5}$-haloalkyl, —$SO_2R'$, —$SO_3H$, —$SO_3M$ (M=alkali metal), —COOR', —CONHR', —CONR'R", —OCOOR', —OCOR', —OCONHR', (meth)acrylamino, (meth)acryloxy; $C_{6-12}$-aryl optionally substituted by $C_{1-12}$-alkyl, $C_{1-12}$-alkoxy, CN and/or by halogen, or $C_{3-12}$-heteroaryl optionally substituted by $C_{1-12}$-alkyl, $C_{1-12}$-alkoxy, CN and/or by halogen, wherein M represents an alkali metal cation, R' and R" represent H, $C_{1-20}$-alkyl, $C_{4-12}$-cycloalkyl; $C_{6-12}$-aryl optionally substituted by $C_{1-12}$-alkyl, $C_{1-12}$-alkoxy, CN and/or by halogen, or $C_{3-12}$-heteroaryl optionally substituted by $C_{1-12}$-alkyl, $C_{1-12}$-alkoxy, CN and/or by halogen, X represents an optionally substituted linear or branched linker of carbon, oxygen, nitrogen, sulfur, phosphorus and/or silicon in the chain, T represents an acrylate radical —O—(C═O)—CH═$CH_2$ or a methacrylate radical —O—(C═O)—C($CH_3$)═$CH_2$, and n represents an integer from 2 to 5.

According to the invention, at least two radicals T are bonded to the linker X according to the general formula (I).

The UV absorbers according to the invention themselves have film-forming properties. On application to the surface of the plastics material they form an amorphous, transparent and clear coating and do not have a tendency to crystallise. In addition, owing to the polymerisable acrylate and/or methacrylate groups, the coatings produced with the UV absorbers according to the invention are thermally or UV-curable or curable by another conventional curing method (e.g. electron beam curing, plasma curing, etc.). Therefore, the UV absorbers according to the invention permit the production of thin and strong layers which absorb UV radiation sufficiently and can offer a resistant base (primer layer) for scratch-resistant lacquers, preferably sol-gel lacquers. Because of the satisfactory UV-protective action of that primer layer, the addition of further UV absorbers to such an outer scratch-resistant lacquer coating is no longer necessary, or at least no longer necessary in relatively large amounts, so that an impairment of the mechanical strength does not have to be accepted either.

Triazines with (meth)acrylate groups have already been described several times (DE-A 197 39 781; EP-A 0 706 083; U.S. Pat. No. 6,500,887; unpublished German patent application DE 10 2009 019493.2). In EP-A 0 706 083, a plurality of triazines each having only one methacrylate group have been described. However, those compounds are crystalline substances which cannot be used as curing lacquers. Such substances have been used in the production of UV-absorbing copolymers. Crystalline triazine with one methacrylate group is also described in U.S. Pat. No. 6,500,887 and was added in the conventional manner to the plastics material to be protected. In DE-A 197 39 781, EP-A 0 706 083, U.S. Pat. No. 6,500,887 and the as yet unpublished German patent application DE 10 2009 019493.2, triazines that comprise a plurality of methacrylate groups have also been described. However, such groups are so distributed in the molecules that only one methacrylate group may be attached to each individual substituent of the hard aromatic colourant core. The disclosed ways of using such substances do not go beyond those for compounds that comprise only one methacrylate group. The use of such substances themselves as curing, film-forming compounds for UV-protective lacquers for the protection of plastics materials is not described.

The compounds according to the invention are therefore novel.

The compounds according to the invention preferably have a UV absorption maximum at from 300 to 340 nm.

In the compounds of the general formula (I), X preferably represents an optionally substituted linear or branched linker, wherein a chain of at least 4 atoms selected from carbon, oxygen, nitrogen, sulfur, phosphorus and/or silicon is present in the chain between the O atom of group A and each T group.

The compounds of the general formula (I) are preferably compounds of the general formula (I-1)

(I-1)

wherein

Z represents an optionally substituted linear or branched $C_{1-20}$-alkylene radical or $C_{1-20}$-alkylene ether radical, and T, n, $Y^1$ and $Y^2$ have the meanings given above for the compounds of the general formula (I).

Of the compounds of the general formula (I-1), particular preference is given to compounds of the general formula (II)

$$A\text{-}C(R^4)H\text{—}C(=O)\text{—}O\text{—}CH_2\text{—}C(R^5)p(CH_2\text{-}T)q \quad (II),$$

wherein $R^4$ represents H or $C_{1-20}$-alkyl, $R^5$ represents H, $C_{1-20}$-alkyl or —$CH_2$—OH, p represents 0 or 1, q represents 3–p.

Of the compounds of the general formula (I) or (I-1), preference is further given to compounds of the general formula (III)

$$A\text{-}C(R^4)H\text{—}C(=O)\text{—}O\text{—}CH_2\text{—}CH(T)\text{-}CH_2\text{-}T \quad (III)$$

wherein $R^4$ represents H or $C_{1-20}$-alkyl.

Of the compounds of the general formula (I) or (I-1), preference is further given to compounds of the general formula (IV)

$$A\text{-}C(R^4)H\text{—}C(=O)\text{—}O\text{—}CH_2\text{—}C(R^5)m(CH_2\text{-}T)n\text{-}$$
$$CH_2\text{—}O\text{—}CH_2\text{—}C(R^5)p(CH_2\text{-}T)q \quad (IV)$$

wherein $R^4$ represents H or $C_{1-20}$-alkyl, $R^5$ represents —$CH_2$—OH, m represents 0 or 1, n represents 2–m and p represents 0, 1 or 2, q represents 3–p.

In formulae (II), (III) and (IV), A and T have the meanings given above for the compounds of the general formula (I).

In preferred embodiments, in the substituents $Y^1$ and $Y^2$ in formulae (I), (I-1) or (II) to (IV), r in each case represents 1.

In preferred embodiments, in the substituents $Y^1$ and $Y^2$ in formulae (I), (I-1) or (II) to (IV), the radicals $R^1$, $R^2$ and $R^3$ in each case represent H.

Particularly preferably, the substituents $Y^1$ and $Y^2$ in formulae (I), (I-1) or (II) to (IV) simultaneously represent
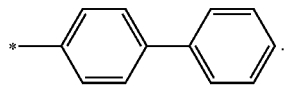
Of the compounds having the general formula (I) or (I-1), the following compounds of formulae (I-1-1) to (I-1-12) are most particularly preferred
(I-1-1)
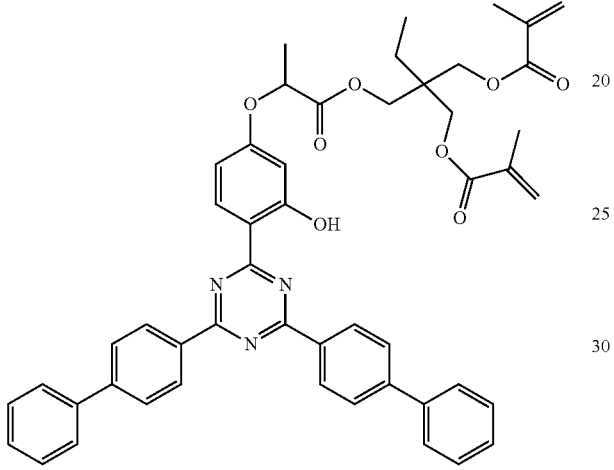
(I-1-2)
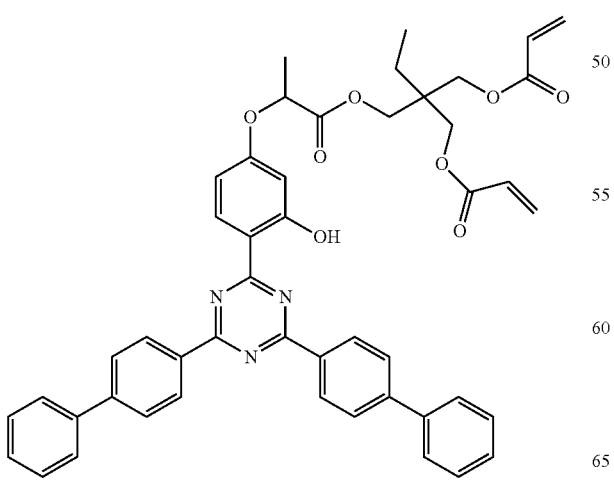
(I-1-3)
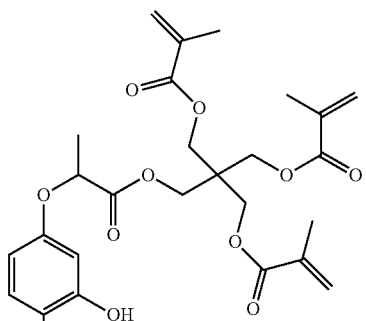
(I-1-4)
(I-1-5)
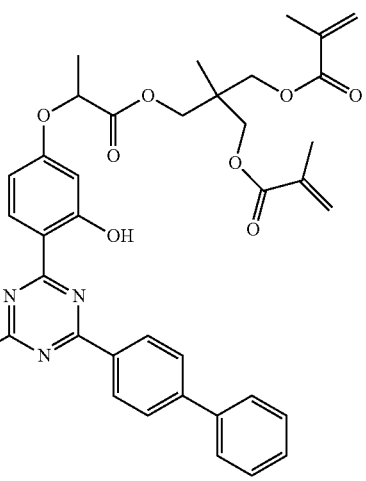

(I-1-6)
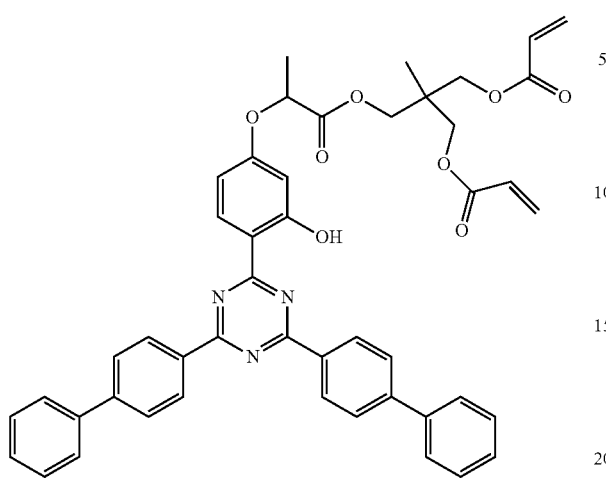
(I-1-7)
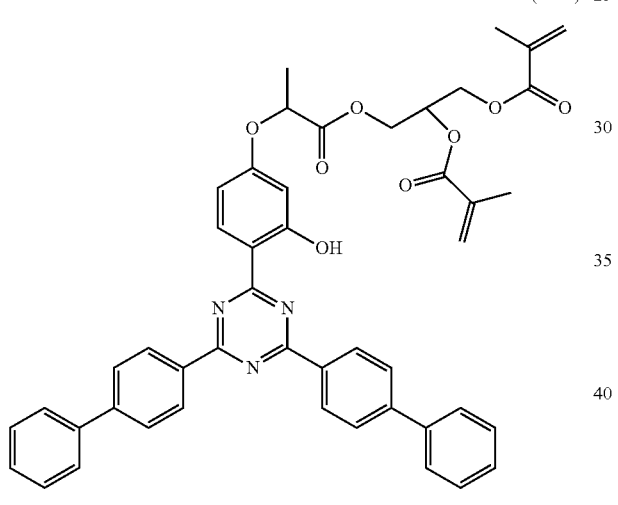
(I-1-8)
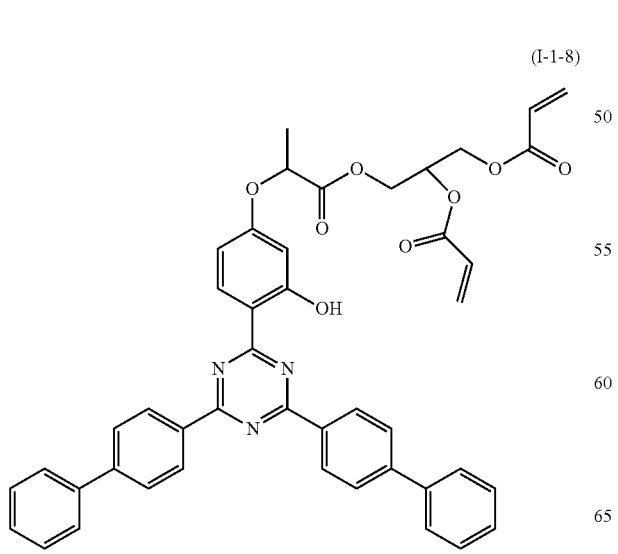
(I-1-9)
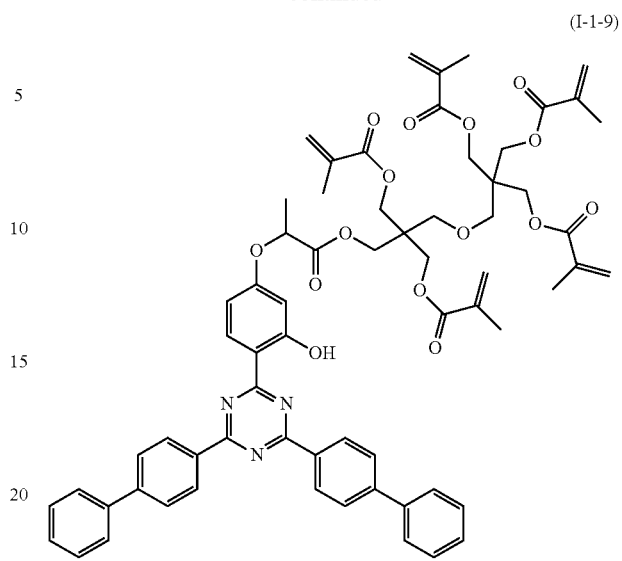
(I-1-10)
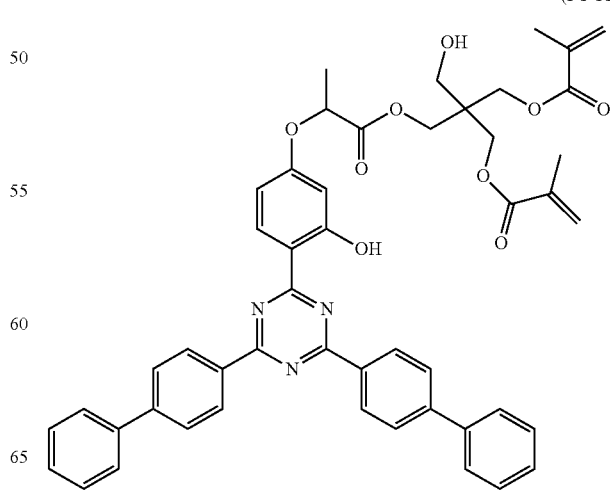
(I-1-11)

(I-1-12)

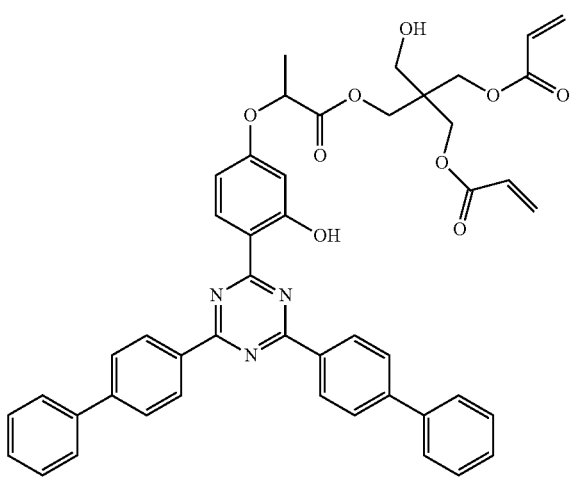

The invention further provides coating compositions which comprise at least one of the UV-absorbing compounds of the general formula (I) according to the invention.

A preferred formulation of the coating composition according to the invention for application of the compounds of the general formula (I) to the surface of plastics materials is a solution in conventional organic solvents.

The coating compositions according to the invention therefore preferably comprise at least one organic solvent. Suitable solvents are, for example, aromatic solvents, ketones, alcohols, ethers or esters, such as, for example, alkyl acetates. Toluene, butyl acetate, diacetone alcohol and 2-methoxypropanol are particularly preferred. The solvent should preferably be matched to the plastics material that is to be coated so that superficial damage, for example by etching, is avoided. For the coating of substrates comprising polycarbonates or copolycarbonates, diacetone alcohol or 2-methoxypropanol is particularly preferred as the solvent.

The coating compositions according to the invention can preferably additionally comprise the initiators of the polymerisation. Preferred initiators are thermally or UV-driven initiators. Conventional peroxides that decompose into radicals above 50° C., such as diacyl peroxides, peroxy dicarbonates, peroxy esters, perketals, hydroxy peroxides, keto peroxides and dialkyl peroxides, can be used as thermal initiators. Suitable thermal initiators are also typical azo initiators.

Suitable UV-driven initiators (photoinitiators) preferably have high photochemical reactivity and an absorption band in the near-UV range (>300 nm and particularly preferably >350 nm).

Suitable photoinitiators are, for example, those selected from the group comprising acylphosphine oxide derivatives and α-aminoalkylphenone derivatives.

There are preferably used as photoinitiators bis(2,4,6-trimethylbenzoyl)phenylphosphine oxide (Irgacure® 819 from Ciba Specialty Chemicals), (2,4,6-trimethylbenzoyl)diphenylphosphine oxide (Lucirin® TPO Solid from BASF AG), bis(2,6-dimethylbenzoyl)(2,4,4-trimethylpentyl)phosphine oxide, bis(2,6-dimethoxybenzoyl)(2,4,4-trimethylpentyl) phosphine oxide, benzoylphosphonic acid bis(2,6-dimethylphenyl) ester (Lucirin® 8728 from BASF AG), 2,4,6-trimethylbenzoylethoxyphenylphosphine oxide (Lucirin® TPO-L from BASF AG), 2-benzyl-2-(dimethylamino)-1-(4-morpholinophenyl)-1-butanone (Irgacure® 369 from Ciba Speciality Chemicals) and 2-methyl-1-[4-(methylthio)phenyl]-2-morpholino-1-propanone (Irgacure® 907 from Ciba Speciality Chemicals).

There are particularly preferably used as photoinitiators bis(2,4,6-trimethylbenzoyl)phenyl-phosphine oxide (Irgacure® 819 from Ciba Specialty Chemicals), 2,4,6-trimethylbenzoyl-ethoxyphenylphosphine oxide (Lucirin® TPO-L from BASF AG) and 2-methyl-1-[4-(methylthio)phenyl]-2-morpholino-1-propanone (Irgacure® 907 from Ciba Speciality Chemicals). Also suitable are mixtures of those photoinitiators with one another and mixtures of the photoinitiators with other generally known photoinitiators such as, for example, α-hydroxyalkyl-phenones or phenylacetophenones. There are preferably used mixtures of bis(2,6-dimethoxy-benzoyl)(2,4,4-trimethylpentyl)phosphine oxide and (I-hydroxycyclohexyl)phenylmethanone, preferably in the ratio 25:75 (Irgacure® 1800 from Ciba Speciality Chemicals), mixtures of 2,4,6-trimethylbenzoyl-diphenyl-phosphine oxide and 2-hydroxy-2-methyl-1-phenyl-1-propanone, preferably in the ratio 50:50 (Darocur 4265 from Ciba Speciality Chemicals) or a mixture of bis(2,6-dimethoxybenzoyl)(2,4,4-trimethylpentyl)phosphine oxide and 2-hydroxy-2-methyl-1-phenyl-1-propanone, preferably in the ratio 25:75 (Irgacure® 1700 from Ciba Speciality Chemicals).

The coating compositions according to the invention can also comprise stabilisers. Preferred stabilisers are so-called HALS (Hindered Amine Light Stabiliser) as basic stabilisers. HALS, that is to say sterically hindered amines, are generally liquid or solid piperidine derivatives of the general formula (V)

(V)

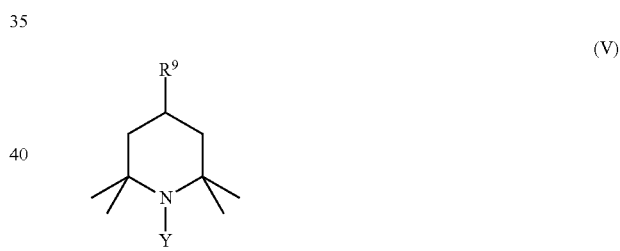

wherein

Y represents H or $CH_3$, and $R^9$ represents $Z—R^{11}$,

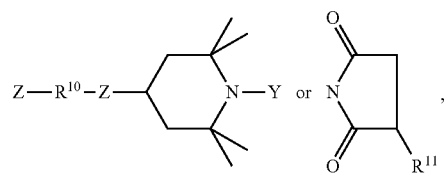

wherein

Z represents a divalent functional group such as, for example and preferably, —C(O)O—, —NH— or —NHC(O)—, $R^{10}$ represents a divalent organic radical such as, for example and preferably, —$(CH_2)_l$—, wherein l represents an integer from 1 to 12, preferably from 3 to 10, —C=CH-Ph-O ($CH_3$)—, and

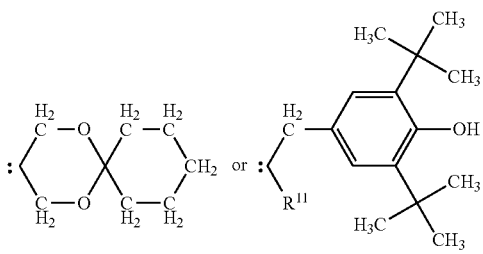

R$^{11}$ represents H or C$_1$-C$_{20}$-alkyl.

Sterically hindered amines act as radical acceptors, which capture the radicals formed on polymer degradation. A general overview of HALS types is given by T. Bolle in Lackadditive, J. Bielemann, ed.; Wiley-VCH: Weinheim (1998) and A. Valet in Lichtschutzmittel für Lacke, Vincentz Verlag Hanover (1996). Preferred HALS are disclosed in publication EP-A 1 308 084 and also DE-A 60 307 122, special mention being made of the combination thereof with the present compounds of the general formula (I).

The compounds of the general formula (I) according to the invention are not crystallisable, and without the addition of further polymerisable comonomers, crosslinkers, oligomeric or polymeric binders and/or thickeners they already form an amorphous and transparent coating, which can be converted into a strong, thin UV-protecting layer by thermal or UV curing or by a further conventional curing method (e.g. electron beam curing, plasma curing, etc.).

In preferred embodiments of the present invention, the coating compositions according to the invention accordingly do not contain any further polymerisable comonomers, crosslinkers, oligomeric or polymeric binders or thickeners.

For certain applications, however, it can be advantageous for the coating compositions according to the invention to comprise, in addition to at least one compound of the general formula (I), also one or more reactive diluents and/or reactive, that is to say polymerisable, oligomeric or polymeric binders. Such reactive diluents and/or oligomeric or polymeric binders are preferably added in an amount of 80 wt. % or less, based on the total weight of the compounds of the general formula (I).

Suitable reactive diluents are known and are described in Chemistry & Technology of UV & EB Formulation for Coatings, Inks & Paints, Vol. 2, 1991, SITA Technology, London (P.K.T: Oldring (Ed.) on p. 237-306 (Reactive Diluents). Preferred reactive diluents are, for example, methanediol diacrylate, 1,2-ethanediol diacrylate, 1,3-propanediol diacrylate, 1,2-propanediol diacrylate, glycerol triacrylate, 1,4-butanediol diacrylate, 1,3-butanediol diacrylate, 1,2,4-butanetriol triacrylate, 1,5-pentanediol diacrylate, neopentyl glycol diacrylate, pentaerythritol triacrylate, pentaerythritol tetraacrylate, 1,6-hexanediol diacrylate, trimethylolpropane diacrylate, trimethylolpropane triacrylate, tricyclodecanedimethanol diacrylate, diethylene glycol diacrylate, triethylene glycol diacrylate, tetraethylene glycol diacrylate, dipropylene glycol diacrylate, tripropylene glycol diacrylate, trimethylolpropanetriethoxy triacrylate, dipentaerythritol pentaacrylate, dipentaerythritol hexaacrylate, ditrimethylolpropane tetraacrylate and the corresponding methacrylate derivatives. 1,6-Hexanediol diacrylate, tricyclodecanedimethanol diacrylate, trimethylolpropane triacrylate, pentaerythritol tetraacrylate and the methacrylate derivatives thereof are particularly preferably used.

Likewise suitable as the optional reactive polymerisable component are oligomeric aliphatic urethane acrylates or polyester acrylates (reactive oligomeric or polymeric binders). The preparation of the suitable oligomers belonging to the class of the aliphatic urethane acrylates or polyester acrylates, and the use thereof as lacquer binders, are known and are described in Chemistry & Technology of UV & EB Formulation for Coatings, Inks & Paints, Vol. 2, 1991, SITA Technology, London (P.K.T: Oldring (Ed.) on p. 73-123 (Urethane Acrylates) and p. 123-135 (Polyester Acrylates). Commercially available substances which are suitable within the scope of the invention are, for example, aliphatic urethane acrylates such as Ebecryl® 4858, Ebecryl® 284, Ebecryl® 265, Ebecryl® 264 (manufacturer in each case Cytec Surface Specialities), Craynor® 925 from Cray Valley, Viaktin® 6160 from Vianova Resin, Roskydal® 2258 from Bayer MaterialScience AG, Photomer 6891 from Cognis, or also aliphatic urethane acrylates dissolved in reactive diluents, such as Laromer® 8987 (70% strength in hexanediol diacrylate) from BASF AG, Desmolux® U680H (80% strength in hexanediol diacrylate) from Bayer MaterialScience AG, Craynor® 945B85 (85% in hexanediol diacrylate) and Craynor® 963B80 (80% in hexanediol diacrylate), in each case from Cray Valley, or polyester acrylates such as Ebecryl® 810 or 830 from Cytec Surface Specialities.

Instead of the optional reactive polymerisable component, commercially available ready-made UV lacquers can also be used. Such lacquers are obtainable, for example, from Momentive Performance Materials under the product names UVHC3000, UVHC3000K; UVHC3000H, UVHC7000, UVHC8558 and UVHC8600.

The coating compositions according to the invention can optionally comprise one or more further additives selected from the group comprising stabilisers, flow agents, surface additives, pigments, colourants, adhesion promoters, IR absorbers, and UV absorbers other than the compounds of the general formula (I).

The coating compositions according to the invention can optionally also comprise inorganic nanoparticles for increasing the mechanical resistance and for additional protection against UV radiation.

Suitable nanoparticles are inorganic oxides, mixed oxides, hydroxides, sulfates, carbonates, carbides, borides and nitrides of elements of main groups II to IV and/or elements of subgroups I to VIII of the periodic system including the lanthanides. Preferred nanoparticles are silicon oxide, aluminium oxide, cerium oxide, zirconium oxide, niobium oxide, zinc oxide or titanium oxide nanoparticles; silicon oxide nanoparticles are particularly preferred.

The particles that are used preferably have mean particle sizes (measured by means of dynamic light scattering in dispersion determined as the Z average) of less than 200 nm, preferably from 5 to 100 nm, particularly preferably from 5 to 50 nm. Preferably at least 75%, particularly preferably at least 90%, most particularly preferably at least 95%, of all the nanoparticles used have the sizes defined above.

The nanoparticles can in principle be used both in powder form and in the form of colloidal suspensions or dispersions in suitable solvents. The inorganic nanoparticles are preferably used in colloidally disperse form in organic solvents (organosols). Suitable solvents for the organosols are, for example, alcohols, such as, for example, methanol, ethanol, isopropanol, ketones, such as, for example, acetone, 2-butanone, methyl isobutyl ketone, diacetone alcohol, esters, such as, for example, butyl acetate, ethyl acetate, 1-methoxy-2-propyl acetate, aromatic solvents, such as, for example, toluene, xylene, and also ethers, such as, for example, 1,4- dioxane, ethylene glycol n-propyl ether, or arbitrary mixtures of such solvents. Suitable organosols have a solids content of from 10 to 60 wt. %, preferably from 15 to 50 wt. %. Suitable organosols are, for example, silicon dioxide organosols as are obtainable, for example, under the trade names Organosilicasol® and Suncolloid® (Nissan Chem. Am. Corp.) or under the name Highlink®NanO G (Clariant GmbH).

The nanoparticles can be surface-modified. Preferably suitable are those inorganic particles that have been modified at the surface by silanisation. That method is known in principle in the literature and is described, for example, in DE-A 19846660 or WO-A 2003/44099. The surface of the inorganic nanoparticles can further be modified adsorptively/associatively by surfactants or block copolymers, for example as in WO-A 2006/008120 or Foerster, S. & Antonietti, M., Advanced Materials, 10, no. 3, (1998) 195. Preferred surface modification is silanisation with alkoxysilanes and/or chlorosilanes. Partial modification with γ-(meth)-acryloxypropyltri(m)ethoxysilane or γ-glycidoxypropyltrimethoxysilane according to WO-A 2004/035474 is particularly preferred.

The coating compositions according to the invention can be prepared in a simple manner by adding the individual components, compound(s) of the general formula (I), optionally initiator(s), stabiliser(s), reactive diluents, binders and other additives, to the solvent or solvents and mixing them together by stirring. Preferably, the compound(s) of the general formula (I) is/are first dissolved in the solvent or solvents, and then the further components are added. Purification by means of filtration is then optionally carried out. The nanoparticles can be added to the coating compositions according to the invention during or after the preparation of the above-described mixture of components. The addition can be effected simply by stirring the particles into the coating compositions according to the invention. However, the use of increased dispersing energy, such as, for example, by means of ultrasound, jet dispersion or high-speed stirrer according to the rotor-stator principle, is also conceivable. Simple mechanical stirring is preferred.

The coating compositions according to the invention are suitable for the production of coatings having a UV-protective action. To that end, the coating compositions according to the invention can be applied by conventional methods to corresponding substrates and then cured under suitable conditions.

Accordingly, the present invention also provides a method of coating substrates, characterised in that
A) a layer of a coating composition according to at least one of claims 6 to 10 is applied to the substrate,
B) then at least part of the solvent is removed from the layer obtained according to step A), and
C) then the layer obtained according to step B) is cured.

Application can be carried out, for example, by dipping, flood coating, spraying, knife application, pouring, spin coating or brush application. Any solvent present is then removed, preferably evaporated off, wholly or partially and the coating so obtained is cured at room temperature or at elevated temperature, by UV light or by another conventional curing method (e.g. electron beam curing, plasma curing, etc.), preferably by UV light. Details regarding application by conventional methods will be found, for example, in Organic Coatings: Science and Technology, John Wiley & Sons 1994, Chapter 22, pages 65-82.

The coatings (C) produced from the UV-protective formulations according to the invention offer very good protection of the substrate against UV radiation and provide long-lasting protection for surfaces against photochemical degradation. They can therefore be used wherever a UV-unstable substrate is to be protected against UV radiation, especially from sunlight or from an artificial radiation source. Many plastics materials, but also natural materials such as wood, can be provided by the coatings according to the invention with long-lasting protection against photochemical degradation. The coating of glass, on the other hand, which is likewise possible, serves not to protect the substrate but to screen against long-wave UV radiation (≥300 nm), which penetrates commercial window glass, for example, almost completely.

Accordingly, the present invention also provides a coating produced from a coating composition according to the invention.

In preferred embodiments, the coatings according to the invention have layer thicknesses of from 0.1 µm to 20 µm, particularly preferably from 0.3 µm to 10 µm, most particularly preferably from 0.5 µm to 5 µm. The higher the content of the compounds of the general formula (I) according to the invention in the coatings according to the invention, the thinner the chosen layer thicknesses can be in order to achieve sufficient UV protection.

The coatings according to the invention preferably have an extinction value at 340 nm—also referred to as the optical density at 340 nm—of 1.2 or more, preferably of 1.5 or more, particularly preferably of 2 or more. That extinction value is a measure of the protective action of the coating according to the invention against UV radiation. The extinction value at 340 nm is measured according to method A mentioned in the examples using a Cary 50 UV-VIS spectrometer from Varian Inc., USA.

Accordingly, the present invention further provides articles characterised in that they have at least one substrate and at least one coating produced from at least one coating composition according to the invention. Suitable substrates are those of plastics material, glass or natural materials, such as, for example, wood. Substrates of plastics material are preferred. The substrate is particularly preferably a moulded article, an extrudate or a coextrudate comprising one or more thermoplastic plastics. Most particularly preferred articles according to the invention are, for example, films, sheets, multi-wall sheets, headlamp cover plates, automotive glazing or architectural glazing.

Accordingly, the coating compositions according to the invention are suitable according to the invention for the coating of surfaces, such as, for example, plastics materials, wood or glass, in particular plastics surfaces. Owing to their high transparency, the coatings according to the invention can in particular also be used on transparent plastics materials, preferably transparent thermoplastics such as polycarbonate, polyacrylate or poly(meth)acrylate, polysulfones, polyesters, thermoplastic polyurethane and polystyrene and also copolymers and mixtures (blends) thereof. Suitable thermoplastics are, for example, polyacrylates, poly(meth)acrylates (e.g. PMMA; e.g. Plexiglas® from Röhm), cycloolefin copolymers (COCs; e.g. Topas® from Ticona; Zenoex® from Nippon Zeon or Apel® from Japan Synthetic Rubber), polysulfones (Ultrason® from BASF or Udel® from Solvay), polyesters, such as, for example, PET or PEN, polycarbonate (PC), polycarbonate/polyester blends, for example PC/PET, polycarbonate/polycyclohexylmethanol-cyclohexane dicarboxylate (PCCD; Xylecs® from GE), polycarbonate/PBT and mixtures thereof. Particularly advantageously, polycarbonates and copolycarbonates, especially bisphenol-A-based (aromatic) polycarbonates and copolycarbonates, are protected against UV radiation by such coatings according to the invention. Polycarbonate so provided with long-lasting protection against UV radiation can then be used, for example, for the glazing of buildings and vehicles, where yellowing must be prevented over long periods. Poly(meth)acrylates and also polycarbonates or copolycarbonates are preferably used, and in particular polycarbonates or copolycarbonates and mixtures thereof are used.

Suitable polycarbonates for the preparation of the plastics composition according to the invention are all known polycarbonates. Those are homopolycarbonates, copolycarbonates and thermoplastic polyester carbonates. The suitable polycarbonates preferably have mean molecular weights $\overline{M}_w$ of from 18,000 to 40,000, preferably from 26,000 to 36,000 and in particular from 28,000 to 35,000, determined by measuring the relative solution viscosity in dichloromethane or in mixtures of equal amounts by weight phenol/o-dichlorobenzene calibrated by light scattering.

The preparation of the polycarbonates is preferably carried out by the interfacial process or the melt transesterification process, which have been described many times in the literature. For the interfacial process, reference is made by way of example to H. Schnell, Chemistry and Physics of Polycarbonates, Polymer Reviews, Vol. 9, Interscience Publishers, New York 1964 p. 33 ff., to Polymer Reviews, Vol. 10, "Condensation Polymers by Interfacial and Solution Methods", Paul W. Morgan, Interscience Publishers, New York 1965, Chap. VIII, p. 325, to Dres. U. Grigo, K. Kircher and P. R. Müller "Polycarbonate" in Becker/Braun, Kunststoff-Handbuch, Volume 3/1, Polycarbonate, Polyacetale, Polyester, Celluloseester, Carl Hanser Verlag Munich, Vienna 1992, p. 118-145 and to EP-A 0 517 044. The melt transesterification process is described, for example, in Encyclopedia of Polymer Science, Vol. 10 (1969), Chemistry and Physics of Polycarbonates, Polymer Reviews, H. Schnell, Vol. 9, John Wiley and Sons, Inc. (1964) and in patent specifications DE-B 10 31 512 and U.S. Pat. No. 6,228,973.

The polycarbonates are obtained from reactions of bisphenol compounds with carbonic acid compounds, in particular phosgene or, in the case of the transesterification process, diphenyl carbonate or dimethyl carbonate. Particular preference is given to homopolycarbonates based on bisphenol A and to copolycarbonates based on the monomers bisphenol A and 1,1-bis-(4-hydroxyphenyl)-3,3,5-trimethylcyclohexane. Further bisphenol compounds which can be used for the polycarbonate synthesis are disclosed inter alia in WO-A 2008037364, EP-A 1 582 549, WO-A 2002026862, WO-A 2005113639.

The polycarbonates can be linear or branched. It is also possible to use mixtures of branched and unbranched polycarbonates.

Suitable branching agents for polycarbonates are known from the literature and are described, for example, in patent specifications U.S. Pat. No. 4,185,009, DE-A 25 00 092, DE-A 42 40 313, DE-A 19 943 642, U.S. Pat. No. 5,367,044 and in literature cited therein. In addition, the polycarbonates that are used can also be intrinsically branched, in which case no branching agent is added within the context of the polycarbonate preparation. An example of intrinsic branchings is so-called Fries structures, as are disclosed in EP-A 1 506 249 for melt polycarbonates.

Chain terminators can additionally be used in the polycarbonate preparation. There are preferably used as chain terminators phenols such as phenol, alkylphenols such as cresol and 4-tert-butylphenol, chlorophenol, bromophenol, cumylphenol or mixtures thereof.

The plastics composition(s) of the substrate layer or substrate layers can comprise additional additives, such as, for example, UV absorbers, IR absorbers and also other conventional processing aids, in particular demoulding agents and flow agents, and also conventional stabilisers, in particular heat stabilisers, and also antistatics, pigments, colourants and optical brightening agents. Different additives or concentrations of additives can be present in each layer. According to the invention, however, additional UV absorbers are not absolutely necessary in the plastics materials that are to be coated and also are preferably not present.

It may, however, be advantageous to use for the substrate layer(s) plastics composition(s) that comprise small amounts of additional UV absorbers. In a preferred embodiment, therefore, there is used as the plastics material polycarbonate that additionally comprises from 0.01 to 0.5 wt. % of one or more UV absorbers from the classes benzotriazole derivatives, dimeric benzotriazole derivatives, triazine derivatives, dimeric triazine derivatives, diaryl cyanoacrylates. Those UV absorbers are preferably different from the compounds of the general formula (I) according to the invention.

In a further embodiment, further substrate layers, for example coextruded layers that may be present, can comprise larger amounts of additives, in particular of UV absorbers.

In the case of substrates of thermoplastic plastics that are to be coated, it is possible to coat especially extruded, coextruded or injection-moulded moulded articles, for example in the form of films, sheets, multi-wall sheets and also predominantly flat substrates. Fields of application are also in the field of 1K and 2K injection-moulded parts, for example in the form of headlamp cover plates, architectural glazing and automotive glazing.

Depending upon the application, the coatings are advantageously applied to one or more sides of the substrates. Flat substrates such as films or sheets can accordingly be coated on one side or on two sides, it being possible in the case of two-sided coating for the coatings to be the same or different.

The articles comprising the coated substrate can additionally comprise further coatings. In addition to the UV-protective coatings there come into consideration as further coatings, for example, IR-absorbing layers, IR-reflecting layers, electrically conductive layers, electroluminescent layers, coloured and printed layers for decorative purposes, electrically conductive printed layers such as are used, for example, for vehicle window heating, optionally also layers containing heating wires, anti-reflection layers, no-drop coatings, anti-fog coatings, anti-fingerprint coatings and/or combinations thereof. Those coatings can be applied or present in the form of intermediate layers and/or outer layers.

In order to improve the adhesion to the substrate or to a further over-lacquered coating, it is possible to use a suitable adhesion promoter which ensures good adhesion of the coatings according to the invention to the substrate or to the further layers. The adhesion promoter can be added to the coating composition according to the invention or is applied as a separate coating over the layer according to the invention. Conventional adhesion promoters are mostly based on polymethacrylates or polyurethanes. In addition to the adhesion-promoting action, the UV protection of the structure as a whole can optionally be increased by additional UV absorbers and further light stabilisers, preferably HALS. The adhesion promoters, or primers, can either be baked on at elevated temperature after flashing off at room temperature (bake-on-bake process) or can be applied by-overcoating directly with the sol-gel solution or with another top lacquer (wet-on-wet process).

The coatings obtained from the mixtures according to the invention can, moreover, be over-lacquered with further coatings, which can serve, for example, to improve the mechanical properties (scratch resistance). It is likewise possible to apply a plasma layer, which can offer additional barrier and scratch protection. The plasma layer is applied by the deposition of reactive species according to the prior art—for example plasma enhanced chemical vapour deposition PECVD, magnetron sputtering (e.g. US-A 2007/104956) or vapour deposition. Such coating methods are known and are described in detail in RenéA. Haefer "Oberflächen- and Dünnschicht-Technologic" Part I Springer-Verlag 1987. Glass-like layers could typically be deposited thereby. However, diamond-like and amorphous carbon layers are also suitable.

Sol-gel lacquers in particular are suitable for the scratch-resistant coating. Sol-gel lacquers within the scope of the present invention are lacquers that are produced by the sol-gel process. The sol-gel process is a process for the synthesis of non-metallic inorganic or hybrid-polymeric materials from colloidal dispersions, the so-called sols.

For example, sol-gel lacquers can be prepared by hydrolysis of aqueous dispersions of colloidal silicon dioxide and an organoalkoxysilane or mixtures of organoalkoxysilanes of the general formula $RSi(OR')_3$, wherein in the organoalkoxysilane(s) of the general formula $RSi(OR')_3$ R represents a monovalent $C_1$-$C_6$-alkyl radical or a wholly or partially fluorinated $C_1$-$C_6$-alkyl radical, a vinyl unit or an allyl unit, an aryl radical or a $C_1$-$C_6$-alkoxy radical. Particularly preferably, R is a $C_1$-$C_4$-alkyl radical, for example a methyl, ethyl, n-propyl, isopropyl, tert-butyl, sec-butyl or n-butyl radical, a vinyl, allyl, phenyl or substituted phenyl radical. The radicals —OR' are selected independently of one another from the group comprising $C_1$-$C_6$-alkoxy groups, a hydroxy group, a formyl group and an acetyl group.

The colloidal silicon dioxide is, for example, obtainable as e.g. Levasil® 200 A, Nalco® 1034A (Nalco Chemical Co), Ludox® AS-40 or Ludox® LS (GRACE Davison). The following compounds may be mentioned as examples of organoalkoxysilanes: 3,3,3-trifluoropropyltrimethoxysilane, methyltrimethoxysilane, methyltrihydroxysilane, methyltriethoxysilane, ethyltrimethoxysilane, methyltriacetoxysilane, ethyltriethoxysilane, phenyltrialkoxysilane (e.g. phenyltriethoxysilane and phenyltrimethoxysilane) and mixtures thereof.

As catalysts for the hydrolysis there can be used, for example, organic and/or inorganic acids or bases.

In one form of the preparation of sol-gel lacquers, the colloidal silicon dioxide particles can also be formed in situ by pre-condensation starting from alkoxysilanes (see in this connection "The Chemistry of Silica", Ralph K. Her, John Wiley & Sons, (1979), p. 312-461).

The hydrolysis of the sol-gel solution is terminated or slowed considerably by addition of solvents, preferably alcoholic solvents such as, for example, isopropanol, n-butanol, isobutanol or mixtures thereof. Then—for example for the UV protection of the sol-gel coating—one or more UV absorbers, which are optionally pre-dissolved in a solvent, can be added to the sol-gel coating solution, following which an ageing step of a few hours or several days/weeks occurs. Furthermore, further additives and/or stabilisers, such as, for example, flow agents, surface additives, thickeners, pigments, colourants, curing catalysts, IR absorbers and/or adhesion promoters, can be added.

The use of hexamethyldisilazane or comparable compounds, which can lead to reduced susceptibility of the coatings to cracking, is also possible (see also WO 2008/109072 A).

As UV absorbers for the sol-gel coatings there can be used, for example, as desired, the commercially available moderately polar, mostly hydroxy-containing UV absorbers and/or inorganic UV absorbers, such as titanium dioxide, zinc oxide or cerium dioxide, which, however, do not have the optimum action (EP-A 0 931 820). UV absorbers modified with an alkoxy-silyl(alkyl) group for such lacquer systems based on resorcinol have been disclosed in U.S. Pat. Nos. 5,391,795 and 5,679,820.

Commercially available UV-stabilised sol-gel lacquers are obtainable, for example, from Momentive Performance Materials under the product names AS4000 and AS4700. At layer thicknesses of from 1 to 20 µm, preferably from 2 to 15 µm, particularly preferably from 4 to 12 µm, sol-gel siloxane lacquers have an extinction of from 0.2 to 4, preferably from 0.2 to 2, particularly preferably 0.3≤extinction (sol-gel layer) ≤1.5.

The coating according to the invention is suitable particularly preferably as a primer layer for scratch-resistant coatings that are applied by means of sol-gel lacquers. The latter exhibit excellent adhesion to the coatings according to the invention. Preferably no additional adhesion promoter layer is necessary therefor.

Hybrid-polymeric lacquers within the scope of the present invention—which are also called hybrid lacquers—are based on the use of hybrid polymers as binders. Hybrid polymers (hybrid: lat. "of dual origin") are polymeric materials that combine structural units of different material classes at the molecular level. As a result of their structure, hybrid polymers can exhibit wholly novel property combinations. Unlike composite materials (defined phase boundaries, weak interactions between the phases) and nanocomposites (use of nano-scale fillers), the structural units of hybrid polymers are linked together at the molecular level. That is achieved by chemical processes such as, for example, the sol-gel process, with which inorganic networks can be built up. By using organically reactive precursors, for example organically modified metal oxides, organic oligomer/polymer structures can additionally be produced. Acrylate lacquers which comprise surface-modified nanoparticles and form an organic/inorganic network after curing are likewise defined as hybrid lacquers.

A possible thermally curable hybrid lacquer is PHC587B or PHC587C (Momentive Performance Materials), see also EP-A 0 570 165. The layer thickness should be from 1 to 20 µm, preferably from 3 to 15 µm, particularly preferably from 6 to 8 µm.

UV-curable hybrid lacquers are, for example, UV-curable acrylate lacquers or UV-curable anhydrous hydrolysable silane systems, as are described in WO 2008/071363 A or DE-A 2804283. A commercially available system is UVHC3000 (Momentive Performance Materials). The layer thickness should be from 1 to 25 µm, preferably from 4 to 20 µm, particularly preferably from 8 to 12 µm. The scratch-proof layers based on hybrid lacquers should have an extinction at 340 nm of from 0.1 to 3, preferably from 0.2 to 2.5, particularly preferably 0.3≤extinction (hybrid layer)≤2. The exemplary embodiments which follow serve to explain the invention by way of example, but without limiting it.

EXAMPLES

Method A: Determination of the Extinction (Determination of the Optical Density) at 340 nm The extinction of the coating according to the invention after application to a polycarbonate substrate (or a glass substrate for method B) and subsequent curing was determined at 340 nm by means of a Cary 50 UV-Vis spectrophotometer from Varian Inc., USA, an uncoated but otherwise identical polycarbonate substrate (glass substrate for method B) being used as background spectrum.

Method B: Determination of the Layer Thickness

For the determination of the layer thickness of the coatings on the polymeric substrates, the lacquer composition in question was applied, for calibration, in different layer thicknesses to glass and cured, the extinction of the coating in question at 340 nm was determined according to method A, and the layer thicknesses of the coatings were determined by means of an Alpha-Step 500 profilometer (Tencor). Then, on the basis of the extinction at 340 nm, determined using method A), of the coating in question on the polycarbonate substrate whose layer thickness was to be determined, the layer thickness of that coating was calculated (the extinction of the coating in question at 340 nm is proportional to the layer thickness of the coating).

Example 1

Preparation of the UV Absorber According to the Invention

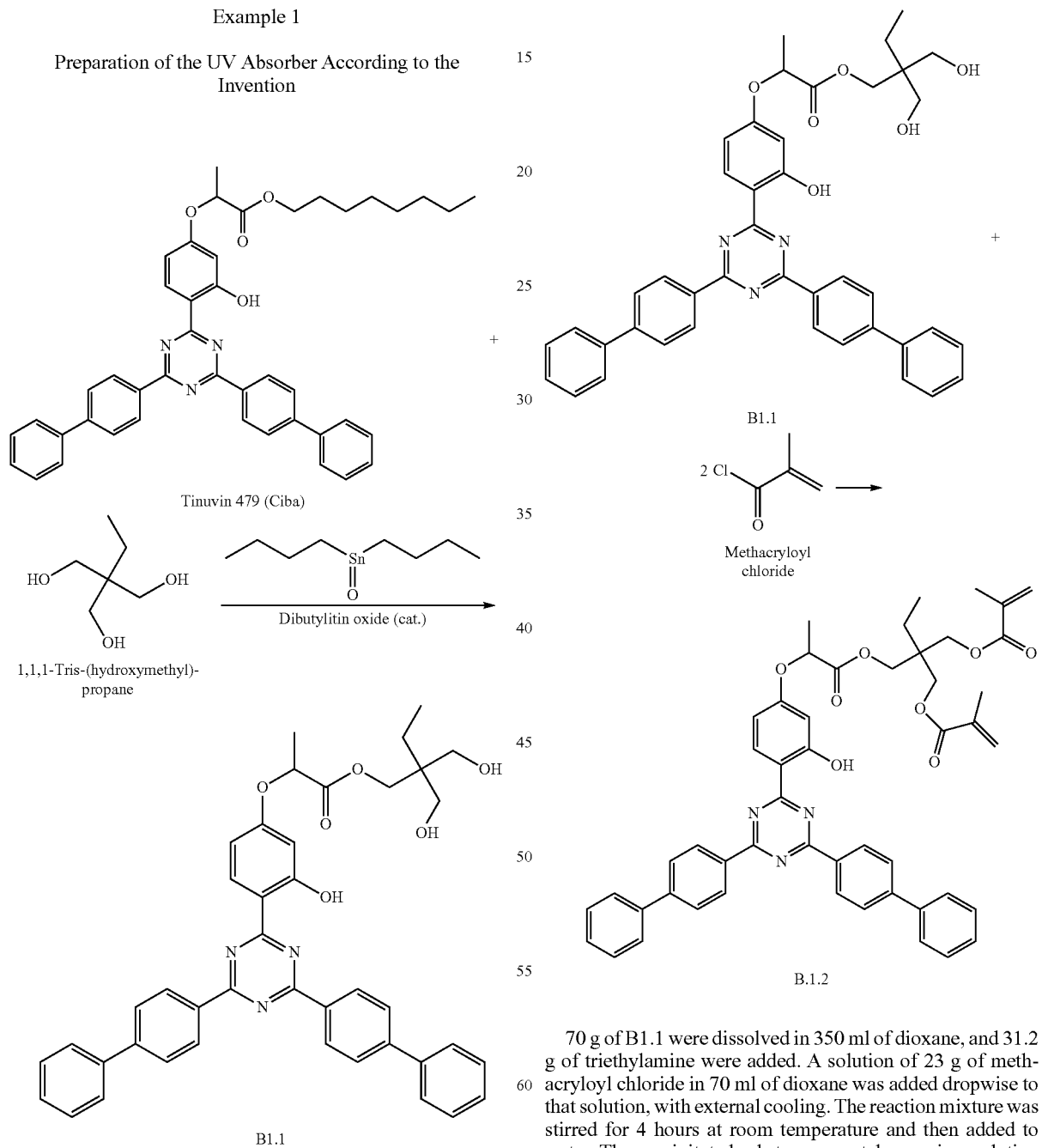

110 g of Tinuvin 479 (Ciba Specialty Chemicals Inc., Switzerland) and 8.1 g of dibutyltin oxide (Aldrich) were placed in 217.7 g of 1,1,1-tris-(hydroxymethyl)-propane (Aldrich) and stirred for 5 hours at 165° C. (temperature of the oil bath). The stirred mass was initially cloudy and then became clear. After cooling of the reaction mixture, the product was precipitated in crystalline form with methanol, filtered off, rinsed with methanol and dried. Further purification was carried out by crystallisation twice from toluene. The melting point of B1.1 is 121.8° C. Yield: 70 g (63% of the theoretical yield).

Elemental analysis: $C_{42}H_{39}N_3O_6$ (681.80)
Calc.: C, 73.99; H, 5.77; N, 6.16.
Found: C, 74.80; H, 6.00; N, 5.90.

70 g of B1.1 were dissolved in 350 ml of dioxane, and 31.2 g of triethylamine were added. A solution of 23 g of methacryloyl chloride in 70 ml of dioxane was added dropwise to that solution, with external cooling. The reaction mixture was stirred for 4 hours at room temperature and then added to water. The precipitated substance was taken up in a solution of toluene and ethyl acetate (8:1). The solution was dried over magnesium sulfate. Subsequent purification by chromatography was carried out on silica gel in toluene/ethyl acetate (8:1). After removal of the solvent, compound B.1.2 was dried in vacuo. The product was a non-crystalline glass-like solid resin. Yield: 29 g (35% of the theoretical yield).

Elemental analysis: $C_{50}H_{47}N_3O_8$ (817.95)
Calc.: C, 73.42; H, 5.79; N, 5.14.
Found: C, 73.20; H, 6.00; N, 5.10.

Example 2

Preparation of the Lacquer Formulations (Coating Compositions) According to the Invention a) 1 g of B.1.2 was added to 9 g of diacetone alcohol and dissolved completely at room temperature. 0.02 g of Darocur® 4265 was added. The clear solution was filtered over a suction filter (membrane filter of pore size 0.2 μm) and transferred to a flask made of dark glass.

b) 0.9 g of B.1.2 and 0.1 g of dipentaerythritol penta-/hexa-acrylate (DPHA, Aldrich) were added to 9 g of diacetone alcohol and dissolved completely at room temperature. 0.02 g of Darocur® 4265 was added. The clear solution was filtered over a suction filter (membrane filter of pore size 0.2 μm) and transferred to a flask made of dark glass.

c) Analogously to b), a further lacquer formulation was prepared from 0.8 g of B.1.2 and 0.2 g of dipentaerythritol penta-/hexa-acrylate (DPHA, Aldrich).

d) Analogously to b), a further lacquer formulation was prepared from 0.5 g of B.1.2 and 0.5 g of dipentaerythritol penta-/hexa-acrylate (DPHA, Aldrich).

e) Analogously to b), a further lacquer formulation was prepared from 0.25 g of B.1.2 and 0.75 g of dipentaerythritol penta-/hexa-acrylate (DPHA, Aldrich).

f) 0.5 g of B.1.2 was added to 6.13 g of diacetone alcohol and dissolved completely at room temperature. 3.33 g of the lacquer UVHC 3000 (Momentive Performance Materials) and 0.04 g of Darocur® 4265 were added. The clear solution was filtered over a suction filter (membrane filter of pore size 0.2 μm) and transferred to a flask made of dark glass.

Example 3

Production of the Coated Polycarbonate Articles 3.1. Substrates and their Preparation:

Optical grade injection-moulded polycarbonate (PC) sheets of Makrolon® M2808 (Bayer Material Science AG; medium-viscosity bisphenol A polycarbonate, MVR 10 g/10 min according to ISO 1133 at 300° C. and 1.2 kg, without UV stabilisation) measuring 10×15×0.32 cm were tempered for one hour at 120° C., rinsed with isopropanol and flashed off.

Optical grade injection-moulded polycarbonate (PC) sheets of the same size of Makrolon® AL2647 (medium-viscosity bisphenol A polycarbonate with UV stabiliser and demoulding agent; MFR 13 g/10 min according to ISO 1133 at 300° C. and 1.2 kg) were prepared analogously.

The laminating films of a polycarbonate (PC) film (Makrofol® DE 1—1 cc, thickness 500 μm) provided with laminating films on both sides were removed from both sides. The films were coated without wet cleaning and without thermal pretreatment.

3.2. Application of the UV-protective Layer According to the Invention a) The liquid lacquer formulation from Example 2a) was applied to the sheets or to the films by means of a Zehntner ZAA 2300 film applicator (9 μm spiral bar-coater, drawing speed 15 mm/s). The coatings were dried briefly and cured under a UV lamp. The BK 150 EBU UV system from Arccure Technologies GmbH (UV radiator 150 D 200, electric power 3 kW, UV dose over the entire spectral range 15 J/cm²) was used for that purpose.

The thickness of the coatings so obtained was from 1 to 2 μm. The optical density was measured at 340 nm (measured using a Cary 50 UV-VIS spectrometer—Varian Inc., USA) and was over 3. The adhesion of the coatings was determined by adhesive tape tear-off (3M® 610 adhesive tape) and by cross-cut (analogously to ISO 2409). The test was passed, that is to say the coating was not torn off at all (rating 0 according to ISO 2409).

b) to e) Lacquer formulations 2b) to 2e) were applied and cured analogously to a). The thickness of the coatings so obtained was from 1 to 2 μm. The optical density at 340 nm was over 2. The adhesion test was passed (rating 0 according to ISO 2409).

f) Lacquer formulation 2f) was applied and cured analogously to a). The thickness of the coating so obtained was 2.9 μm. The adhesion test was passed (rating 0 according to ISO 2409). The optical density at 340 nm was 3.76.

3.3 Application of the Top Lacquer Layer:

a) The sheets or films provided with the UV-protective layer from Example 3.2a) were then coated with a commercially available PMMA primer (primer SHP470 from Momentive Performance Materials), flashed off for 30 minutes at room temperature and cured for 30 minutes at 127° C. Immediately thereafter, they were over-lacquered by the flood coating process with the freshly filtered commercially available sol-gel lacquer AS4700 from Momentive Performance Materials. After flashing off for 30 minutes at room temperature, the sheets were cured for one hour at 127° C.

The adhesion of the coatings was determined by adhesive tape tear-off (3M® 610 adhesive tape) and by cross-cut (analogously to ISO 2409). The test was passed, that is to say the coating was not torn off at all (rating 0 according to ISO 2409).

b) The sheets or films provided with the UV-protective layer from Example 3.2a) were then over-lacquered with a commercially available lacquer UVHC 3000 from Momentive Performance Materials by the flood coating process. After flashing off for 6 minutes in a drying cabinet at 70° C., the sheets or films were cured under a UV lamp. The coating passed the adhesion test, that is to say the coating was not torn off at all (rating 0 according to ISO 2409).

c) The sheets provided with the UV-protective layer from Example 3.2e) were then introduced into a vacuum chamber and secured about 180 mm in front of the plasma source. The vacuum chamber was then evacuated to a base pressure of less than $1 \times 10^{-4}$ mbar. A flow of 24 g/h of hexamethylsiloxane was then established and the plasma was ignited with a power of 2000 W, pulsed $T_{on}$=5 ms and $T_{off}$=5 ms. The layer deposition was carried out for 1 minute at a pressure of p=0.025 mbar. The oxygen was then switched on and the flow was increased from 0 to 1 liter/minute over a period of 30 seconds. At a flow of 24 g/h HMDSO and 1 liter/minute $O_2$, layer deposition was carried out for a further 8 minutes at the above-mentioned power at a pressure of p=0.14 mbar. This resulted in a total layer thickness of about 5 μm. The layer was transparent and had a pencil hardness of 3H. The coating passed the adhesion test, that is to say the coating was not torn off at all (rating 0 according to ISO 2409).

The examples show that the UV absorbers according to the invention themselves have film-forming properties and do not require additional film-forming agents, such as, for example, binders or polymerisable comonomers, to form a clear, thin, highly adhesive layer (see in particular examples with coating formulation from Example 2a)). The addition of different amounts of reactive diluents in Examples 2b) to 2e) shows comparable results. The examples further show that the substrates provided with UV protection by the coating according to the invention can be over-lacquered to provide scratch-resistant properties by plasma or with commercially available UV-curing or sol-gel formulations. In addition, it has been possible to show that the coatings according to the invention can themselves be used directly as primer layers for the scratch-resistant coatings without the adhesion being impaired as a result.

The invention claimed is:

1. A compound of the general formula (I)

A-X(-T)$_n$     (I), wherein
A represents

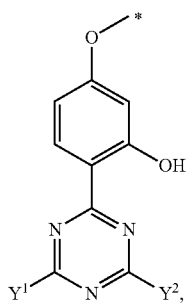

wherein
$Y^1$ and $Y^2$ independently of one another represent substituents of the general formula

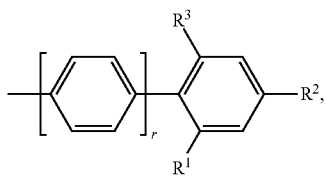

wherein
r represents 0 or 1,
$R^1$, $R^2$, $R^3$ independently of one another represent H, OH, $C_{1-20}$-alkyl, $C_{4-12}$-cycloalkyl, $C_{2-20}$-alkenyl, $C_{1-20}$-alkoxy, $C_{4-12}$-cycloalkoxy, $C_{2-20}$-alkenyloxy, $C_{7-20}$-aralkyl, halogen, —C≡N, $C_{1-5}$-haloalkyl, —SO$_2$R', —SO$_3$H, —SO$_3$M (M=alkali metal), —COOR', —CONHR', —CONR'R'', —OCOOR', —OCOR', —OCONHR', (meth)acrylamino, (meth)acryloxy; $C_{6-12}$-aryl optionally substituted by $C_{1-12}$-alkyl, $C_{1-12}$-alkoxy, CN and/or by halogen, or $C_{3-12}$-heteroaryl optionally substituted by $C_{1-12}$-alkyl, $C_{1-12}$-alkoxy, CN and/or by halogen, wherein
M represents an alkali metal cation,
R' and R'' represent H, $C_{1-20}$-alkyl, $C_{4-12}$-cycloalkyl; $C_{6-12}$-aryl optionally substituted by $C_{1-12}$-alkyl, $C_{1-12}$-alkoxy, CN and/or by halogen, or $C_{3-12}$-heteroaryl optionally substituted by $C_{1-12}$-alkyl, $C_{1-12}$-alkoxy, CN and/or by halogen,
X represents an optionally substituted linear or branched open-chain linker of carbon, oxygen, nitrogen, sulfur, phosphorus and/or silicon in the chain,
T represents an acrylate radical —O—(C=O)—CH=CH$_2$ or a methacrylate radical —O—(C=O)—C(CH$_3$)=CH$_2$, and
n represents an integer from 2 to 5.

2. The compound according to claim 1, wherein the compound is of the general formula (I-1)

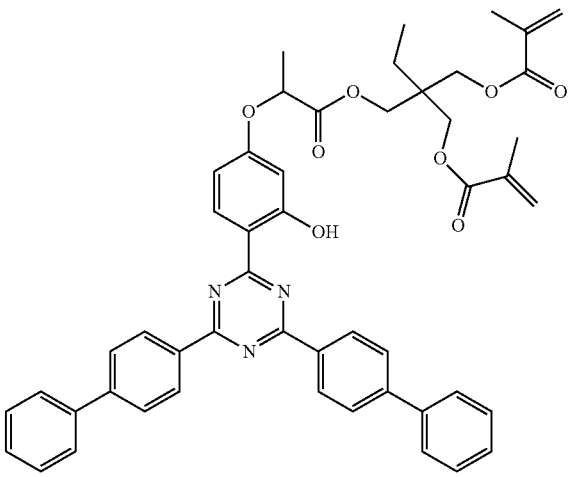

wherein
Z represents an optionally substituted linear or branched $C_{1-20}$-alkylene radical or $C_{1-20}$-alkylene ether radical.

3. The compound according to claim 1, wherein in the substituents $Y^1$ and $Y^2$, r in each case represents 1.

4. The compound according to claim 1, wherein in the substituents $Y^1$ and $Y^2$, the radicals $R^1$, $R^2$ and $R^3$ in each case represent H.

5. The compound according to claim 1, wherein the compound is of formulae from (I-1-1) to (I-1-12)

(I-1-2)
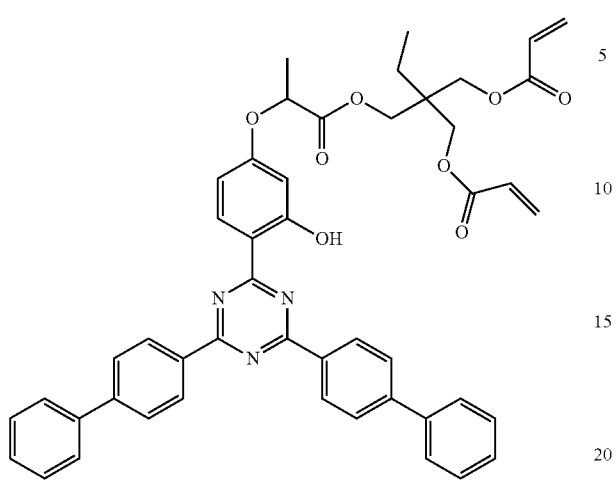
(I-1-3)
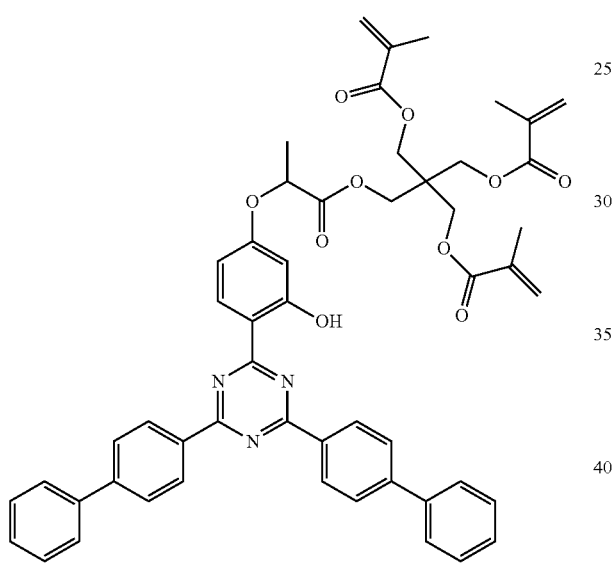
(I-1-4)
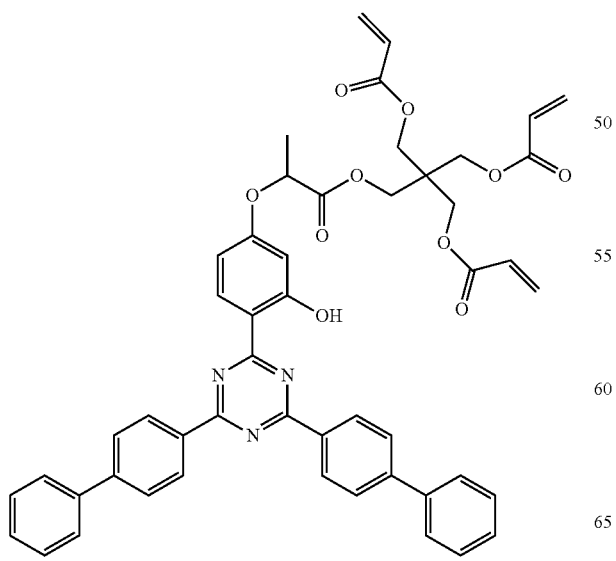
(I-1-5)
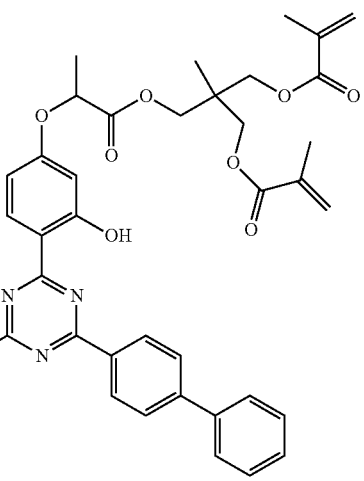
(I-1-6)
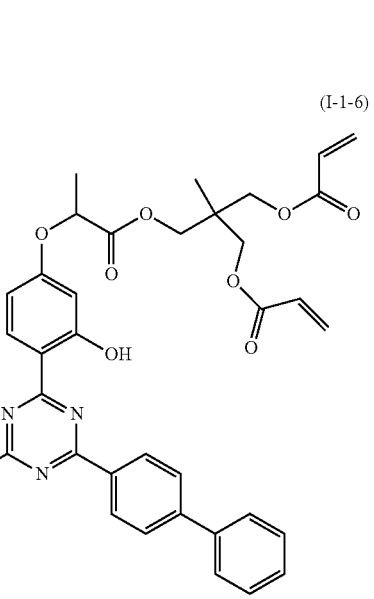
(I-1-7)
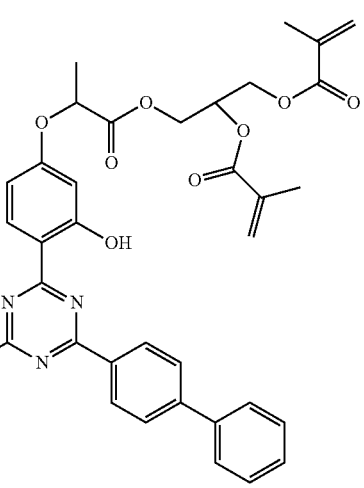

-continued

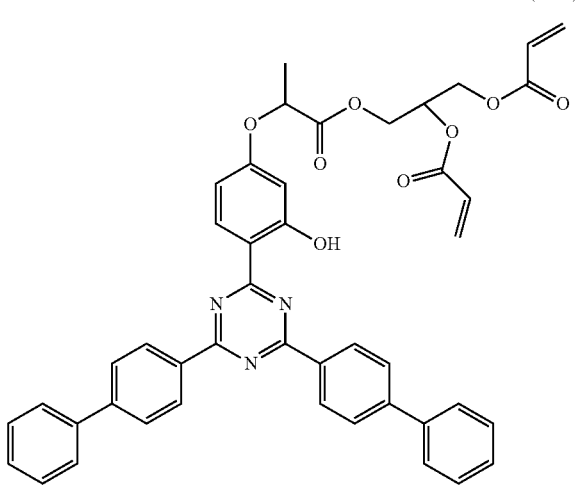
(I-1-8)

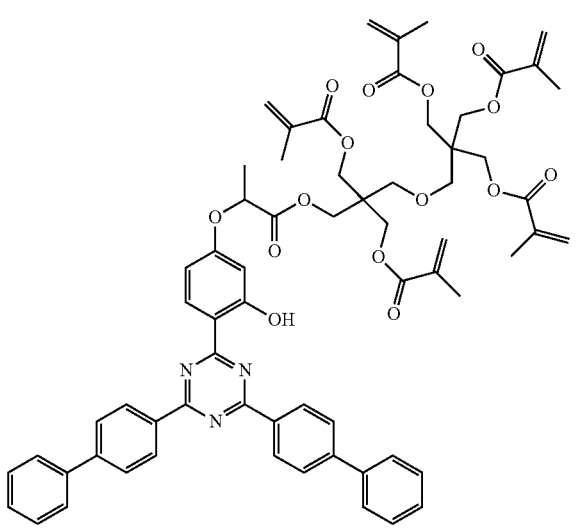
(I-1-9)

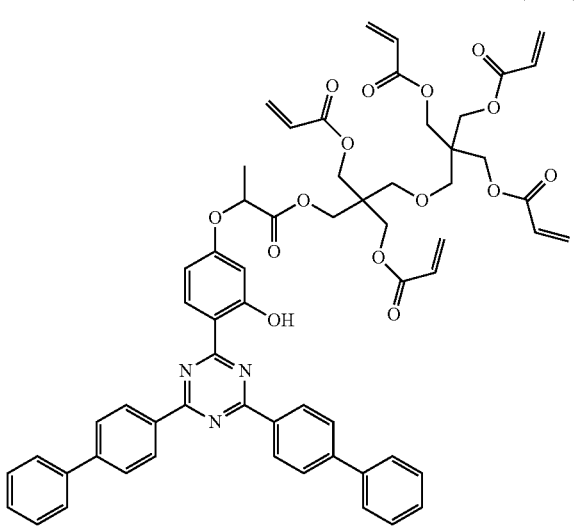
(I-1-10)

-continued

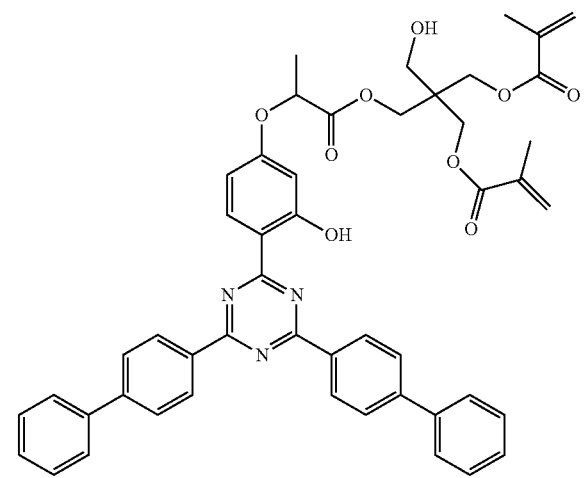
(I-1-11)

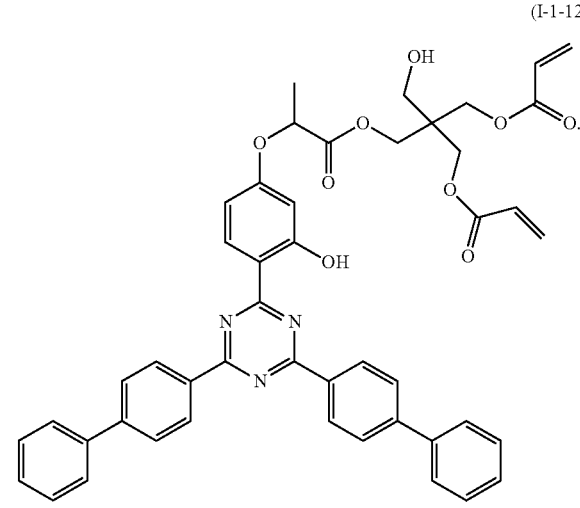
(I-1-12)

6. A coating composition comprising at least one compound according to claim 1 and at least one organic solvent.

7. The coating composition according to claim 6, further comprising at least one initiator.

8. The coating composition according to claim 7, wherein the at least one initiator is a photoinitiator.

9. The coating composition according to claim 6, further comprising at least one stabilizer from the group of Hindered Amine Light Stabilizers (HALS).

10. The coating composition according to claim 6, further comprising at least one reactive diluent or at least one oligomeric aliphatic urethane acrylate or polyester acrylate.

11. The coating composition according to claim 6, further comprising one or more further additives selected from the group consisting of stabilizers, flow agents, surface additives, pigments, colorants, adhesion promoters, IR absorbers, and UV absorbers other than the compounds of the general formula (I).

12. A method of coating a substrate, comprising
  A) applying the coating composition according to claim 6 to the substrate to form a layer,
  B) removing at least part of the at least one organic solvent from the layer obtained according to step A), and
  C) curing the layer.

13. A coating produced from the coating composition according to claim 6.

14. An article, comprising at least one substrate and at least one coating produced from at least one coating composition according to claim 6.

15. The article according to claim 14, wherein the at least one substrate is a moulded article, an extrudate or a coextrudate comprising one or more thermoplastic plastics.

16. The article according to claim 14, wherein the article is a film, a sheet, a multi-wall sheet, a headlamp cover plate, an automotive glazing or an architectural glazing.

* * * * *